United States Patent
Wilson et al.

(10) Patent No.: US 11,986,509 B2
(45) Date of Patent: *May 21, 2024

(54) OLIGOSACCHARIDE FORMULATIONS OF KAPPA OPIOID RECEPTOR AGONISTS

(71) Applicant: CARA THERAPEUTICS, INC., Stamford, CT (US)

(72) Inventors: Bryan R. Wilson, Brewster, NY (US); Stephen J. O'Connor, Guilford, CT (US)

(73) Assignee: Cara Therapeutics, Inc., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/204,986

(22) Filed: Mar. 18, 2021

(65) Prior Publication Data

US 2021/0290723 A1  Sep. 23, 2021

Related U.S. Application Data

(60) Provisional application No. 62/991,560, filed on Mar. 18, 2020.

(51) Int. Cl.

| | | |
|---|---|---|
| A61K 38/07 | (2006.01) | |
| A61K 9/16 | (2006.01) | |
| A61K 9/48 | (2006.01) | |
| A61K 9/50 | (2006.01) | |
| A61K 31/40 | (2006.01) | |
| A61K 31/485 | (2006.01) | |

(52) U.S. Cl.
CPC ............ *A61K 38/07* (2013.01); *A61K 9/1617* (2013.01); *A61K 9/1623* (2013.01); *A61K 9/1694* (2013.01); *A61K 9/4808* (2013.01); *A61K 9/5089* (2013.01); *A61K 31/40* (2013.01); *A61K 31/485* (2013.01)

(58) Field of Classification Search
CPC .... A61K 38/07; A61K 9/1617; A61K 9/1623; A61K 9/1694; A61K 9/4808; A61K 9/5089; A61K 31/40; A61K 31/485
See application file for complete search history.

(56) References Cited

U.S. PATENT DOCUMENTS

| | | |
|---|---|---|
| 6,187,330 B1 * | 2/2001 | Wang .................. A61P 9/00 |
| | | 514/777 |
| 7,402,564 B1 | 7/2008 | Schteingart et al. |
| 7,785,631 B2 | 8/2010 | Roser et al. |
| 7,956,028 B2 | 6/2011 | Garigapati et al. |
| 8,377,863 B2 | 2/2013 | Stern et al. |
| 8,592,366 B2 | 11/2013 | Stern et al. |
| 8,664,178 B2 | 3/2014 | Stern et al. |
| 9,302,010 B2 | 4/2016 | Petrelski et al. |
| 9,399,017 B2 | 7/2016 | Stern et al. |
| 10,028,916 B2 | 7/2018 | Broman et al. |
| 11,033,629 B2 | 6/2021 | Wilson et al. |
| 2016/0271124 A1 | 9/2016 | Lebon et al. |
| 2018/0036247 A1 * | 2/2018 | Haruta .................. A61K 31/48 |
| 2018/0078605 A1 * | 3/2018 | Spencer ................ C07K 5/101 |
| 2018/0344831 A1 | 12/2018 | Tanaka et al. |
| 2019/0111001 A1 | 4/2019 | Feng et al. |
| 2019/0241610 A1 * | 8/2019 | Schteingart ............ A61P 1/14 |
| 2020/0009061 A1 * | 1/2020 | Shigeta ................ A61K 9/2054 |

FOREIGN PATENT DOCUMENTS

WO        2008064353 A    5/2008

* cited by examiner

*Primary Examiner* — Robert A Wax
*Assistant Examiner* — Olga V. Tcherkasskaya
(74) *Attorney, Agent, or Firm* — Algis Anilionis; Anilionis Intellectual Property Law, LLC

(57) ABSTRACT

The invention provides formulations for oral delivery of a therapeutic agent wherein the formulation comprises a kappa opioid receptor agonist, an oligosaccharide stabilizing agent and an optional absorption enhancer. The kappa opioid receptor agonist may be coated with, embedded in or mixed with an oligosaccharide, such as trehalose. Also provided are capsules containing the oral formulations of the kappa opioid receptor agonists, the oligosaccharide and the absorption enhancer of the invention. The invention further provides methods of manufacture of the formulations and methods of their use for the prophylaxis, inhibition and treatment of variety of kappa opioid receptor-associated diseases and conditions such as pain, pruritus and inflammation. The methods of use include administering to the mammal the formulation of the kappa opioid receptor agonist, oligosaccharide and optional absorption enhancers.

11 Claims, 6 Drawing Sheets

OLIGOSACCHARIDE FORMULATIONS OF KAPPA OPIOID RECEPTOR AGONISTS

FIELD OF THE INVENTION

The invention relates to a formulation for oral delivery of a therapeutic agent. The formulation includes a therapeutic agent in the form of an active pharmaceutical ingredient (API) and a stabilizing agent, such as an oligosaccharide. Suitable active pharmaceutical ingredients include kappa opioid receptor agonists, such as D-amino acid peptide amides.

The invention also provides a method of manufacture of a formulation for oral delivery of a kappa opioid receptor agonist, the method includes coating the kappa opioid receptor agonist, or a mixture of the kappa opioid receptor agonist and an oligosaccharide, such as trehalose onto a solid surface, such as the surface of a solid bead to produce a releasably bound kappa opioid receptor agonist on the solid surface of the bead. The bead may be further coated with one or more pharmaceutically acceptable absorption enhancers, binder, diluents or excipients, and may also include an enteric coating to provide for protection of the formulation in acidic conditions and dissolution of the formulation under intestinal physiological conditions.

Alternatively, the formulation for oral delivery of the kappa opioid receptor agonist can be produced from spray dried particles formed from a mixture of an oligosaccharide, such as trehalose, with the kappa opioid receptor agonist. In one embodiment, the kappa opioid receptor agonist is embedded in a particle of the oligosaccharide. The particle can also include or be coated with one or more pharmaceutically acceptable absorption enhancers, binder, diluents or excipients, and may also include an enteric coating.

The invention further relates to methods of prophylaxis, inhibition or treatment of kappa opioid receptor-associated diseases and conditions in a human patient or other mammal, the method comprising administering to the patient or the mammal the oral formulation of the invention.

BACKGROUND

Kappa opioid receptor agonists are a novel class of therapeutic agents that have unique physicochemical properties leading to the need for new formulations for efficient delivery and sufficient bioavailability for efficacy of prophylaxis, inhibition or treatment of kappa opioid receptor-associated diseases and conditions. The novel class of kappa opioid receptor agonists includes the synthetic peptide amides disclosed in U.S. Pat. Nos. 7,402,564, 7,713,937, 7,842,662 and 10,550,140. Other kappa opioid receptor agonists include asimadoline (N-[(1S)-2-[(3S)-3-hydroxy-pyrrolidin-1-yl]-1-phenylethyl]-N-methyl-2,2-diphenylac-etamide), as well as nalfurafine ((2E)-N-[(5α,6β)-17-(cyclo-propylmethyl)-3,14-dihydroxy-4,5-epoxymorphinan-6-yl]-3-(3-furyl)-N-methylacrylamide).

Pharmaceutical formulations can be tailored for different delivery routes, such as for intra venous or intra muscular injection, for topical application, inhalation or for oral administration. Each of these formulations must meet the particular stability requirements that permit storage for a period of time after manufacture and before administration to the patient. In certain circumstances the different components of the formulation may interact over time resulting in a reduction in long term stability. Suitable formulations and additives for maximizing bioavailability of particular kappa opioid receptor agonists are unpredictable.

SUMMARY OF THE INVENTION

The invention provides a formulation for oral delivery of a therapeutic agent that includes a kappa opioid receptor agonist as an active pharmaceutical ingredient (API) and a stability agent, such as an oligosaccharide. In one embodiment, the stabilizing agent renders the API in the formulation stable to storage over extended periods of time, such as over a year at ambient temperatures; alternatively, the stabilizing agent renders the kappa opioid receptor agonist in the formulation stable to storage at elevated temperatures, such as 40° C. for several months. In another embodiment, the formulation of the invention includes a kappa opioid receptor agonist and a stabilizing agent, such as an oligosaccharide, and an absorption enhancer.

The invention further provides a formulation that is a bioactive composition that includes a biologically active peptide embedded in an oligomeric saccharide forming a particle including the stabilized biologically active peptide. Alternatively, the bioactive composition that includes a biologically active peptide can be mixed with an oligosaccharide and coated onto a solid particle or bead. The coated particle or bead can be enteric coated.

The biologically active peptide can be any suitable biologically active peptide, such as for instance a biologically active peptide that includes one or more D-amino acids. In one embodiment, the biologically active peptide that includes one or more D-amino acids is a kappa opioid receptor agonist. The biologically active peptide kappa opioid receptor agonist that includes one or more D-amino acids can be any suitable biologically active peptide kappa opioid receptor agonist that includes one or more D-amino acids such as for instance, and without limitation, any of the peptide kappa opioid receptor agonists disclosed in U.S. Pat. No. 7,402,564. In one embodiment, the biologically active peptide kappa opioid receptor agonist that includes one or more D-amino acids is (D-Phe-D-Phe-D-Leu-D-Lys-[ω(4-aminopyperidine-4-carboxylic acid)]-OH also known as CR845, as disclosed and identified as compound 2 in U.S. Pat. No. 7,402,564.

In one embodiment the invention provides a formulation for oral delivery of a kappa opioid receptor agonists, wherein the formulation comprises a particle including a kappa opioid receptor agonist and an oligosaccharide. The kappa opioid receptor agonist can be (i) CR845 having the formula:

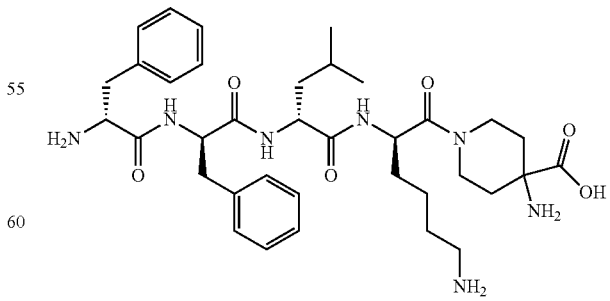

D-Phe-D-Phe-D-Leu-D-Lys-[ω(4-aminopiperidine-4-carboxylic acid)]-OH or a hydrate, salt, acid salt or acid salt hydrate of CR845;

(ii) asimadoline (N-[(1S)-2-[(3S)-3-hydroxy-pyrrolidin-1-yl]-1-phenylethyl]-N-methyl-2,2-diphenylacetamide), or
(iii) nalfurafine ((2E)-N-[(5α,6β)-17-(cyclopropylmethyl)-3,14-dihydroxy-4,5-epoxymorphinan-6-yl]-3-(3-furyl)-N-methylacrylamide). and the oligosaccharide can be suitable oilgosaccharides, such as for instance, trehalose, sucrose, maltose, mannose, lactose and inulin.

In another embodiment of the invention, the formulation for oral delivery of a therapeutic agent, interchangeably referred to herein as the oral formulation of the invention, includes a peptide amide kappa opioid receptor agonist which contains one or more D-amino acids and stabilizing agent, such as an oligosaccharide and one or more absorption enhancers. The peptide amide kappa opioid receptor agonist which contains one or more D-amino acids can be any suitable peptide amide containing at least one D-amino acid, such as for instance, but not limited to, any of the synthetic peptide amides disclosed in U.S. Pat. Nos. 7,402,564, 7,713,937 and 7,842,662 to Schteingart et al., the entire disclosures of which are herein incorporated by reference.

In another embodiment, the bioactive composition includes a biologically active peptide embedded in an oligomeric saccharide forming a particle including the stabilized biologically active peptide, wherein the oligomeric saccharide includes a disaccharide. The disaccharide can be any suitable disaccharide, such as for instance, a disaccharide that includes one or more glucose monomers. In one embodiment, the disaccharide includes trehalose, the 1,1-α-glycoside linked glucose dimer. In a particular embodiment the disaccharide can consist entirely of trehalose.

In one embodiment, the bioactive composition includes a biologically active peptide embedded in an oligomeric saccharide to form a particle including the stabilized biologically active peptide, wherein the oligomeric saccharide enhances the stability of the biologically active peptide over at least a year at 25° C.

In another embodiment of the oral formulation of the invention, the oral formulation includes a peptide amide kappa opioid receptor agonist, an oligosaccharide and one or more absorption enhancers, wherein the peptide amide kappa opioid receptor agonist has a structure of the following formula:

$$Xaa_1—Xaa_2—X_{aa3}—X_{aa4}\text{-}(G)$$ Formula I wherein G is an amide group as described in any U.S. Pat. Nos. 7,402,564, 7,713,937 and 7,842,662.

In another embodiment the oral formulation of the invention includes a peptide amide kappa opioid receptor agonist and one or more absorption enhancers, wherein the peptide amide kappa opioid receptor agonist is CR845 having the structure of the following formula Formula II

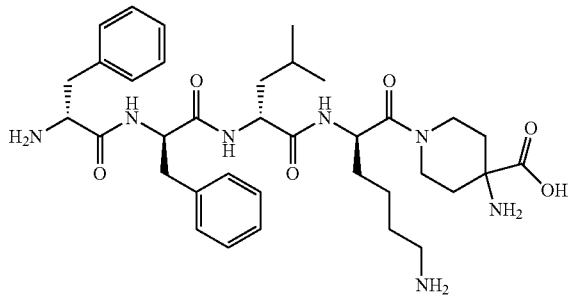 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC(N)(C(=O)O)CC1]

D-Phe-D-Phe-D-Leu-D-Lys-[ω(4-aminopiperidine-4-carboxylic acid)]-OH or a hydrate, salt or acid salt hydrate thereof.

In still another embodiment, the oral formulation of the invention may further include one or more absorption enhancers, binders, surfactants, chelating agents, and pharmaceutically acceptable excipients or diluents.

In one embodiment, the invention provides a method of manufacture of a formulation for oral delivery of a kappa opioid receptor agonist, the method includes spray drying a mixture of a kappa opioid receptor agonist and an oligosaccharide to form particles formed of the kappa opioid receptor agonist embedded in the oligosaccharide. The particles may be formulated in a tablet, a caplet, a capsule, a powder, a slurry, a liquid suspension or a gel.

The invention also provides a method of manufacture of a formulation for oral delivery of a kappa opioid receptor agonist, the method includes coating the kappa opioid receptor agonist, or a mixture of the kappa opioid receptor agonist and an oligosaccharide, such as trehalose onto a solid surface, such as the surface of a solid bead or microbead to produce a releasably bound kappa opioid receptor agonist on the solid surface of the bead or microbead.

The bead or microbead coated with a kappa opioid receptor agonist according to the invention can be formed from any pharmaceutically suitable material such as, for instance and without limitation: microcrystalline cellulose; sucrose particle compositions (e.g., Suglets®, Colorcon, Chalfont, PA, which are uniform drug layering pellets, made of sucrose and starch, for immediate, delayed, sustained or extended release dosage forms, with low friability, consistent sphericity, tight particle size control and high batch-to-batch uniformity; Pharm-a-Spheres™ Tornesch, Germany, sugar spheres characterized by outstanding mechanical stability for further processing, providing a suitable carrier for sustained-release formulations). Other suitable particles for coating with kappa opioid receptor agonist compositions include Mannitol pellets and Tartaric acid pellets, (Pharmatrans SANAQ AG, Basel-Allschwil, Switzerland).

One or ore of the oligosaccharide-embedded kappa opioid receptor agonist-coated beads or microbeads may also be coated with one or more pharmaceutically acceptable absorption enhancers, binder, chelating agents, diluents or excipients, and may also include an enteric coating to provide for protection of the formulation in acidic conditions and dissolution of the formulation at intestinal physiological conditions, e.g. pH 5.5-6.0. Alternatively, one or more of the oligosaccharide-embedded kappa opioid receptor agonist-coated beads or microbeads maybe encapsulated in an enteric coated capsule for oral delivery.

The present invention further provides methods of use of a formulation for oral delivery of a therapeutic agent that includes a kappa opioid receptor agonist and an absorption enhancer for the prophylaxis, inhibition or treatment of kappa opioid receptor-associated diseases and conditions in a human patient or other mammal, the method comprising administering to the patient or the mammal the formulation of the invention. In one embodiment, the formulation of the invention includes an oligosaccharide, such as for instance, trehalose. the administered formulation may further include one or more binders, surfactants, chelating agents, and pharmaceutically acceptable excipients or diluents and one or more absorption enhancers suitable for optimizing uptake of the kappa opioid receptor agonist from the gastrointestinal system and thereby enhancing its biological activity. The administered formulation may further include one or more binders, surfactants, chelating agents, and pharmaceutically acceptable excipients or diluents and one or more absorption enhancers suitable for optimizing uptake of the kappa opioid receptor agonist from the gastrointestinal system and thereby enhancing its biological activity.

The invention also provides a method of prophylaxis, inhibition or treatment of a kappa opioid receptor agonist-associated disease or condition, the method includes administering to a patient or other mammal suffering from the kappa opioid receptor agonist-associated disease or condition, an oral formulation that includes a kappa opioid receptor agonist and a stabilizing agent, such as an oligosaccharide. In another embodiment, the method includes administering an oral formulation including a kappa opioid receptor agonist and a stabilizing agent, such as an oligosaccharide, and an absorption enhancer. The administered oral formulation may further include one or more binders, surfactants, chelating agents, and pharmaceutically acceptable excipients or diluents and one or more absorption enhancers suitable for optimizing uptake of the kappa opioid receptor agonist from the gastrointestinal system and thereby enhancing its biological activity.

DETAILED DESCRIPTION OF THE INVENTION

Figure 1:
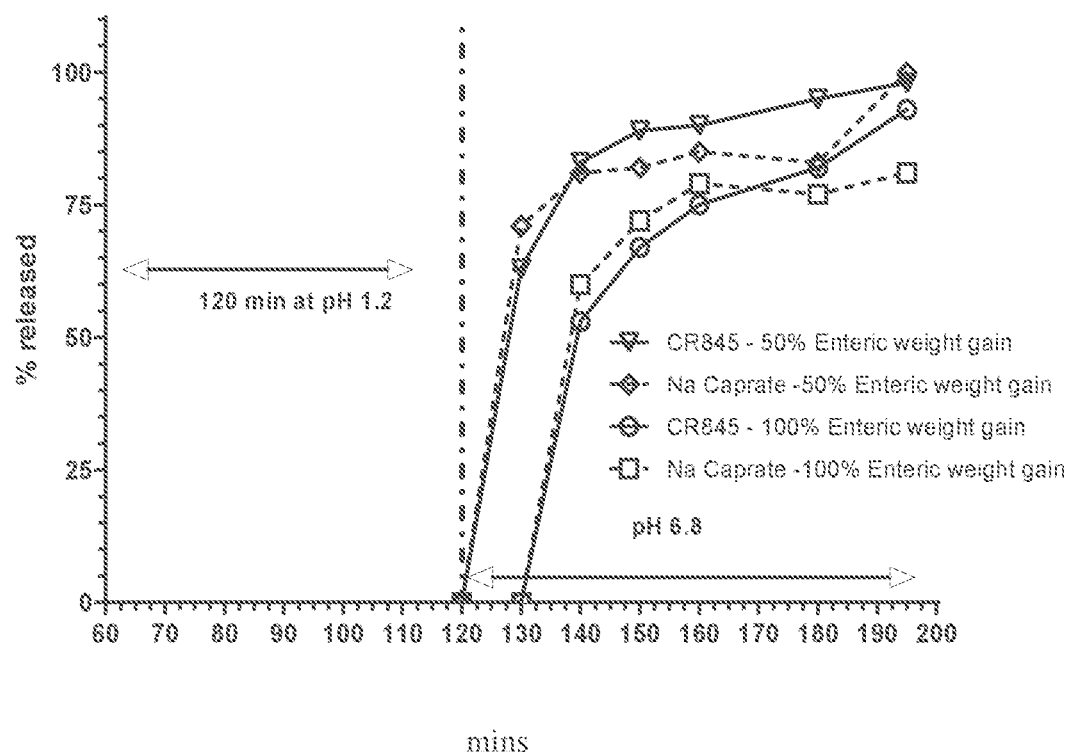
FIG. 1 shows the dissolution profile of enterically coated CR845 Suglet pellets and enterically coated sodium caprate Suglet pellets over time.
Figure 2:
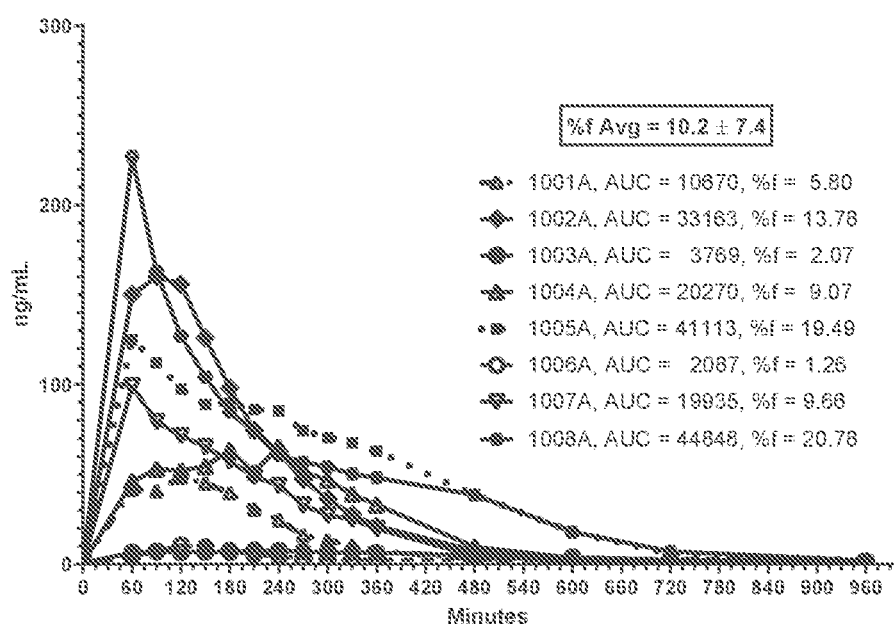
FIGS. 2-6 show the bioactivity profiles of the trehalose-embedded CR845 coated onto composite particles A-E respectively, from Example 3 after administration to eight canine subjects for each composite.
Figure 3:
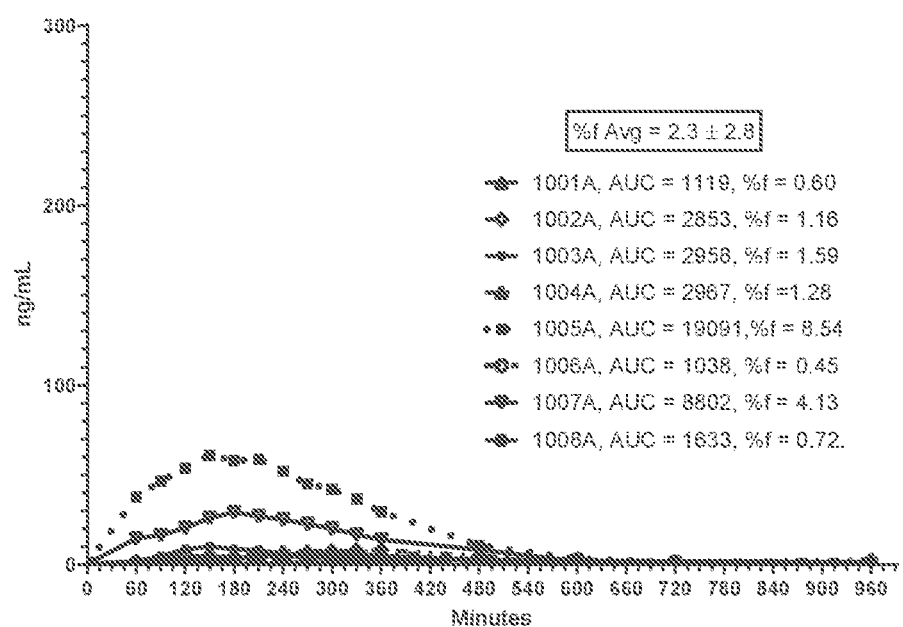
Figure 4:
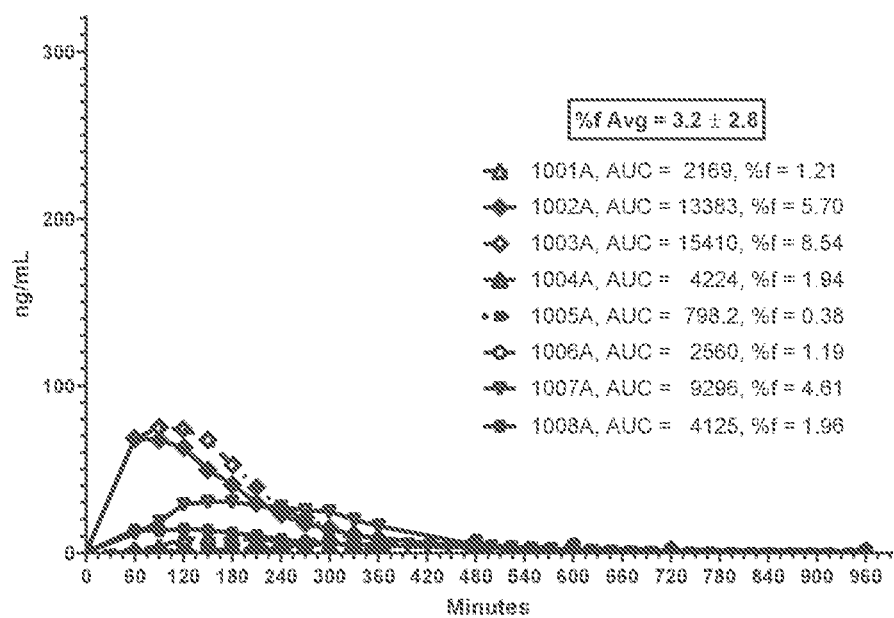
Figure 5:
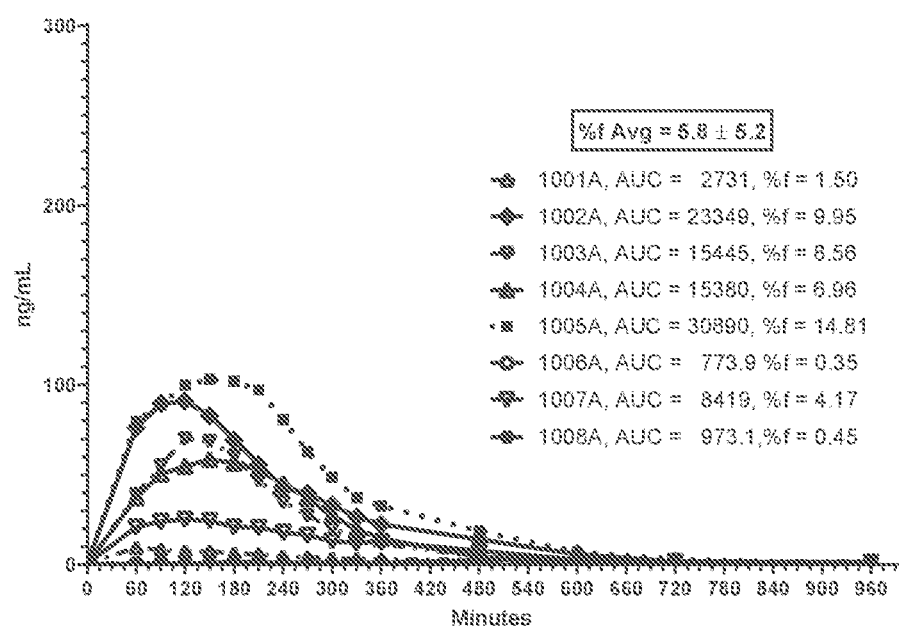
Figure 6:
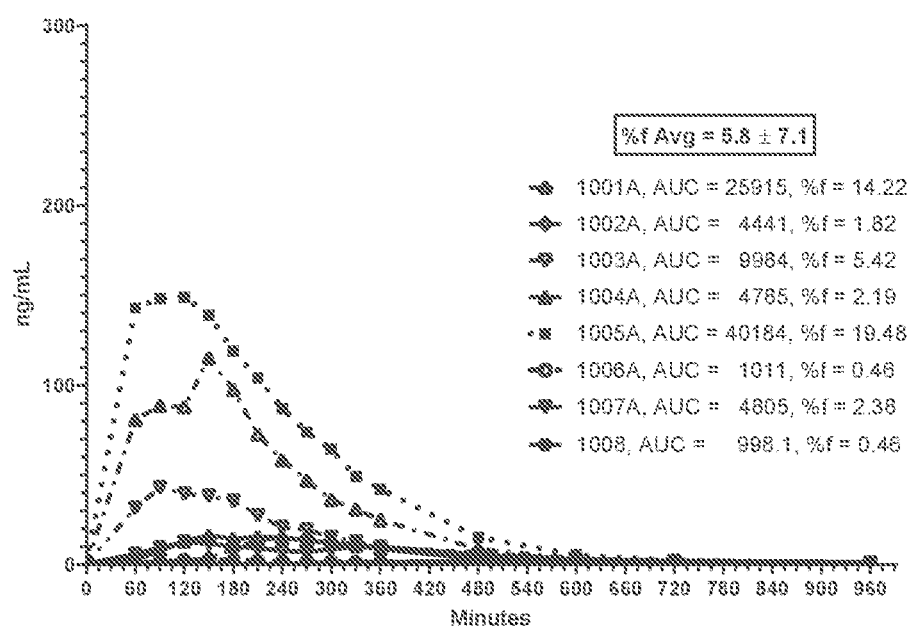

In one embodiment, the oral formulation of the invention includes a therapeutic agent comprising a kappa opioid receptor agonist peptide and an oligosaccharide stabilizing agent. The oligosaccharide stabilizing agent can be any suitable oligosaccharide stabilizing agent, such as for instance an without limitation, maltose, sucrose, lactose and trehalose. In one embodiment the kappa opioid receptor agonist can be optionally embedded in a particle matrix of an oligomeric saccharide, such as for example, the 1,1 α-glucose dimer, trehalose (α-D-glucopyranosyl-(1→1)-α-D-glucopyranoside. In one embodiment the kappa opioid receptor agonist can be optionally mixed with the oligomeric saccharide or embedded in a particle matrix formed of an oligomeric saccharide or can form a formulation layer, coating a solid matrix, such as a bead or microbead. The coating of the kappa opioid agonist and the oligomeric saccharide can be achieved by spray drying a solution containing both the kappa opioid agonist and the oligomeric saccharide in a volatile solvent to form solid particles or the solution can be sprayed onto any desired solid, to form a coating of the kappa opioid agonist and the oligomeric saccharide on the solid surface. In one example, the solid surface can be any suitable solid surface, such as the surface of a bead or microbead and the oligomeric saccharide is trehalose.

In one embodiment the invention provides a formulation that includes the kappa opioid receptor agonist CR845 and the disaccharide, trehalose. The formulation may further include one or more of a pH adjuster, such as a carboxylic acid or a salt of a carboxylic acid, an absorption enhancer, a binding agent, a chelating agent and a pharmaceutically acceptable carrier or excipient.

In another embodiment, the formulation includes CR845 and trehalose further includes citric acid or sodium citrate, a chelating agent such as EDTA (Ethylenediamine-tetraacetic acid) and an absorption enhancer such as lauroyl L-carnitine or sodium caprate. In one embodiment, the citric acid can be a coated citric acid such as powdered 2',7'-Dichlorofluorocein 20 (DCF 20) coated citric acid.

The formulation of the invention can be in the form of a pharmaceutically acceptable tablet, caplet, capsule, powder, slurry or liquid suspension and may be flavored or included in for example, apple sauce or fruit juice for pediatric use.

In another embodiment the invention provides a method of manufacture of a formulation for oral delivery of a kappa opioid receptor agonist, the method includes: Spray drying or spray coating an atomized mixture of the kappa opioid receptor agonist and an oligosaccharide onto one or more solid particles to form kappa opioid receptor agonist/trehalose-coated solid particles; and forming an enteric coating on the kappa opioid receptor agonist/trehalose-coated solid particles to produce a formulation that includes one or more kappa opioid receptor agonist/trehalose-coated solid particles having an enteric coating.

In another embodiment the invention provides a dosage form of a formulation for oral delivery of a therapeutic agent, wherein the formulation includes a kappa opioid receptor agonist, an oligosaccharide and one or more absorption enhancers in a capsule, a caplet, a tablet, a powder or a gel. The enteric coated capsule can be a capsule with an enteric coating or a capsule of a composition having intrinsic enteric properties. An example of a composition having intrinsic enteric properties is the polymer, HPMC, hydroxypropylmethylcellulose.

In another embodiment, the oral formulation of the invention includes a kappa opioid receptor agonist peptide, an oligosaccharide stabilizing agent and at least one absorption enhancer. The absorption enhancer can be any suitable absorption enhancer. Examples of suitable absorption enhancers that can be added include are a hydrophilic surfactant such as for instance Polyoxyethylene 20 sorbitan mono-oleate, sold under the trademark Tween® 80, Polyoxyethylene 20 sorbitan monostearate sold under the trademark Tween® 60, PEG-8-caprylic/capric glycerides sold under as Labrasol® ALF, PEG-35 glyceryl ricinoleate sold as Kolliphor® EL, PEH-15 hydroxystearate sold as Kolliphor® HS 15 and Lauroyl PEG-32 mono/di-tri-glycerides sold as Gelucare® 44/14. Other examples of suitable absorption enhancers that can be added include are a hydrophobic absorption enhancers such as for instance, Capmul® MCM, Captex® 100, Captex® 200 and Capryol® PGMC and tryptophan; and amphiphilic absorption enhancers such as quaternary ammonium salts of fatty acid glycols and chitosan, e.g. quaternary ammonium palmitoyl glycol chitosan.

In one embodiment, the formulation of the invention includes a kappa opioid receptor agonist that includes one or more D-amino acids, an oligosaccharide stabilizing agent and at least one absorption enhancer, the formulation can be in the form of a gel, a capsule, or tablet, wherein the formulation further includes a pharmaceutically acceptable diluent, an excipient or a carrier. In one embodiment the capsule is an enteric coated capsule or a capsule having intrinsic enteric properties.

In one embodiment, the formulation of the invention includes a kappa opioid receptor agonist such as but not limited to asimadoline (N-[(1S)-2-[(3S)-3-hydroxypyrrolidin-1-yl]-1-phenylethyl]-N-methyl-2,2-diphenylacetamide), or nalfurafine ((2E)-N-[(5α,6β)-17-(cyclopropylmethyl)-3,14-dihydroxy-4,5-epoxymorphinan-6-yl]-3-(3-furyl)-N- methylacrylamide), or any of the tetrapeptide amide kappa opioid receptor agonists disclosed in U.S. Pat. No. 10,550,150, and optionally, one or more absorption enhancers. The optional absorption enhancers can be one or more of the many suitable absorption enhancers, such as any one or more of the hydrophilic surfactants, hydrophobic absorption enhancers and amphiphilic absorption enhancers described above.

In one embodiment of the invention, the formulation that includes kappa opioid receptor agonist and absorption enhancer(s) also includes an oligosaccharide, such as for instance, trehalose. The oligosaccharide can be a coating or mixed with the kappa opioid receptor agonist and in some embodiments can be provided in a sufficient amount such that the kappa opioid receptor agonist is embedded or substantially embedded in the oligosaccharide. In one embodiment about 1%-50% of the kappa opioid receptor agonist is embedded in about 50%-99% (w/w) trehalose. Alternatively, about 2%-25% of the kappa opioid receptor agonist is embedded in about 75%-98% (w/w) trehalose. In another embodiment, about 5%-15% of the kappa opioid receptor agonist is embedded in about 85%-95% (w/w) trehalose. In still another embodiment, about 10% of the kappa opioid receptor agonist is embedded in about 90% (w/w) trehalose.

In another embodiment of the invention, the formulation that includes kappa opioid receptor agonist and absorption enhancer(s) also includes a medium chain fatty acid or a salt of a medium chain fatty acid, and a medium chain fatty acid glyceride.

In another embodiment, the oral formulation of the invention includes a therapeutic agent comprising a peptide, and at least one absorption enhancer, the absorption enhancer includes a medium chain fatty acid or a salt of a medium chain fatty acid, and a medium chain fatty acid glyceride, wherein the medium chain fatty acid or the salt of the medium chain fatty acid comprises capric acid or a salt of capric acid, wherein the formulation does not includes a stabilizer, such as polyvinylpyrolidine (PVP). Surprisingly, the formulations of the invention have been found to be effective without the use of PVP or other such stabilizers.

Also provided is a method of treating or preventing a kappa opioid receptor-associated disease or condition in a mammal. The method includes administering to the mammal a composition that includes an effective amount of the above-described formulation of the invention.

The nomenclature used to define the peptides and D-amino acid peptides of the formulations of the invention is specified by Schroder & Lubke, *The Peptides,* Academic Press, 1965, wherein, in accordance with the conventional representation, the N-terminus appears to the left and the C-terminus to the right. Where an amino acid residue has isomeric forms, both the L-isomer form and the D-isomer form of the amino acid are intended to be covered unless otherwise indicated. Amino acids are commonly identified herein by the standard three-letter code. The D-isomer of an amino acid is specified by the prefix "D-" as in "D-Phe" which represents D-phenylalanine, the D-isomer of phenylalanine. Similarly, the L-isomer is specified by the prefix "L-" as in "L-Phe."

As used herein, a kappa opioid receptor-associated disease, condition or disorder is any disease, condition or disorder that is preventable or treatable by activation of a kappa opioid receptor. In some embodiments, a particular oral dose of the formulation of the invention that includes the kappa opioid receptor agonist peptide amide can be chosen by a clinician to completely prevent or cure the disease, condition or disorder. In other embodiments a particular oral dose of the formulation of the invention that includes the kappa opioid receptor against peptide amide chosen by the clinician ameliorates or reduces one or more symptoms of the disease, condition or disorder.

As used herein, "effective amount" or "sufficient amount" of the of the formulation of the invention that includes the kappa opioid receptor agonist peptide amide included in the formulation of the invention refers to an amount of the formulation as described herein that may be therapeutically effective to inhibit, prevent, or treat a symptom of a particular disease, disorder, condition, or side effect.

As used herein, "pharmaceutically acceptable" refers to compounds, materials, compositions, and/or dosage forms which are, within the scope of sound medical judgment, suitable for contact with the tissues of human beings and animals without severe toxicity, irritation, allergic response, or other complications, commensurate with a benefit-to-risk ratio that is reasonable for the medical condition being treated.

As used herein, "dosage unit" refers to a physically discrete unit suited as unitary dosages for a particular individual or condition to be treated. Each unit may contain a predetermined quantity of the formulation of the invention comprising the active kappa opioid receptor agonist peptide amide calculated to produce the desired therapeutic effect(s), optionally in association with a pharmaceutical carrier. The specification for the dosage unit forms may be dictated by (a) the unique characteristics of the active kappa opioid receptor agonist peptide amide, and the particular therapeutic effect to be achieved, and (b) the limitations inherent in the art of compounding such active kappa opioid receptor agonist peptide amide. The dosage unit is often expressed as weight of compound per unit body weight, for instance, in milligrams of compound per kilogram of body weight of the subject or patient (mg/kg). Alternatively, the dosage can be expressed as the amount of the compound per unit body weight per unit time, (mg/kg/day) in a particular dosage regimen. In a further alternative, the dosage can be expressed as the amount of compound per unit body surface area ($mg/m^2$) or per unit body surface area per unit time ($mg/m^2$/day).

As used herein, a "pharmaceutically acceptable salt" refers to a derivative of a compound wherein the parent compound is modified by making an acid or a base salt thereof. Examples of pharmaceutically acceptable salts include, but are not limited to, mineral or organic acid salts of basic residues such as amines; alkali or organic salts of acidic residues such as carboxylic acids and the like. The pharmaceutically acceptable salts include the conventional non-toxic salts or the quaternary ammonium salts of the parent compound formed, for example, from non-toxic inorganic or organic acids. For instance, such conventional non-toxic salts include those derived from inorganic acids such as hydrochloric, hydrobromic, sulfuric, sulfamic, phosphoric, nitric acids and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, furmaric, toluenesulfonic, methanesulfonic, ethane disulfonic, oxalic, isethionic acids, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine. Thus, a pharmaceutically acceptable salt of a synthetic peptide amide can be formed from any such peptide amide having either acidic, basic or both functional groups. For example, a peptide amide having a carboxylic acid group, may be in the presence of a pharmaceutically suitable base, form a carboxylate anion paired with a cation such as a sodium or potassium cation. Similarly, a peptide amide having an amine functional group may, in the presence of a pharmaceutically suitable acid such as HCl, form a salt.

An example of a pharmaceutically acceptable solvate of a kappa opioid receptor agonist peptide amide is a combination of a peptide amide with solvent molecules which yields a complex of such solvent molecules in association with the peptide amide. Combinations of a drug and propylene glycol (1,2-propanediol) have been used to form pharmaceutically drug solvates. See for example U.S. Pat. No. 3,970,651. Other suitable solvates are hydrates of drug compounds. Such hydrates include hydrates which either have comparable activity or hydrates which are converted back to the active compound following administration. A pharmaceutically acceptable N-oxide of a synthetic peptide amide is such a compound that contains an amine group wherein the nitrogen of the amine is bonded to an oxygen atom.

A pharmaceutically acceptable crystalline, isomorphic crystalline or amorphous form of a kappa opioid receptor agonist peptide amide useful in the formulations of the invention can be any crystalline or non-crystalline form of a pharmaceutically acceptable acidic, basic, zwitterionic, salt, hydrate or any other suitably stable, physiologically compatible form of the kappa opioid receptor agonist peptide amide according to the invention.

The kappa opioid receptor agonist peptide amide in the formulations of the invention can be incorporated into pharmaceutical compositions. The compositions can include an effective amount of the kappa opioid receptor agonist peptide amide in a pharmaceutically acceptable diluent, excipient or carrier. Conventional excipients, carriers and/or diluents for use in pharmaceutical compositions are generally inert and make up the bulk of the preparation. The pharmaceutical excipient or carrier can be any compatible, non-toxic substance suitable as a vehicle for delivery the synthetic peptide amide of the invention. Suitable excipients or carriers include, but are not limited to, sterile water (preferably pyrogen-free), saline, phosphate-buffered saline (PBS), water/ethanol, water/glycerol, water/sorbitol, water/polyethylene glycol, propylene glycol, cetylstearyl alcohol, carboxymethylcellulose, corn starch, lactose, glucose, microcrystalline cellulose, magnesium stearate, polyvinylpyrrolidone (PVP), citric acid, tartaric acid, oils, fatty substances, waxes or suitable mixtures of any of the foregoing.

The pharmaceutical composition according to the invention can be formulated as a liquid, semisolid or solid dosage form. For example the pharmaceutical preparation can be in the form of a solution, drops, syrup, spray, suspension, gel, emulsion or in a particulate form, such as pellets or granules, optionally pressed into tablets or lozenges, packaged in capsules or suspended in a liquid. The tablets can contain binders, lubricants, diluents, coloring agents, flavoring agents, wetting agents and may be enteric-coated to survive the acid environment of the stomach and dissolve in the more alkaline conditions of the intestinal lumen. Alternatively, the tablets can be sugar-coated or film coated with a water-soluble film. Pharmaceutically acceptable adjuvants, buffering agents, dispersing agents, and the like, may also be incorporated into the pharmaceutical compositions.

Binders include for instance, starch, mucilage, gelatin and sucrose. Lubricants include talc, lycopodium, magnesium and calcium stearate/stearic acid. Diluents include lactose, sucrose, mannitol, salt, starch and kaolin. Wetting agents include propylene glycol and sorbitan monostearate.

For oral administration, an active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of mediation over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. To facilitate drug stability and absorption, peptides of the invention can be released from a capsule after passing through the harsh proteolytic environment of the stomach.

The active ingredient may be administered all at once, or may be divided into a number of smaller doses to be administered at intervals of time, or as a controlled release formulation. The term "controlled release formulation" encompasses formulations that allow the continuous delivery of a synthetic peptide amide of the invention to a subject over a period of time, for example, several days to weeks. Such formulations may be administered subcutaneously or intramuscularly and allow for the continual steady state release of a predetermined amount of compound in the subject over time. The controlled release formulation of kappa opioid receptor agonist peptide amide may be, for example, a formulation of drug containing polymeric microcapsules, such as those described in U.S. Pat. Nos. 4,677,191 and 4,728,721, incorporated herein by reference. The concentration of the pharmaceutically active compound is adjusted so that administration provides an effective amount to produce a desired effect. The exact dose depends on the age, weight and condition of the patient or animal, as is known in the art. For any particular subject, specific dosage regimens can be adjusted over time according to the individual need and the professional judgment of the person administering or supervising the administered of the formulations. Thus, the concentration ranges set forth herein are exemplary only and are not intended to limit the scope or practice of the claimed invention.

The compositions can be administered or prophylaxis or treatment of individuals suffering from, or at risk of a disease or a disorder. Prophylaxis is defined as a measure designed to preserve the health of an individual. For therapeutic applications, a pharmaceutical composition is typically administered to a subject suffering from a disease or disorder, in an amount sufficient to inhibit, prevent, or ameliorate the disease or disorder. An amount adequate to accomplish this is defined as a "therapeutically effective dose."

The pharmaceutical formulations of the invention can be administered to a mammal for prophylactic or therapeutic purposes. The mammal can be any mammal, such as a domesticated or feral mammal, or even a wild mammal. The mammal can be any primate, ungulate, canine or feline. For instance, and without limitation, the mammal may be a pet or companion animal, such as a dog or a cat; a high-value mammal such as a thoroughbred horse or a show animal, a farm animal, such as a cow, a goat, a sheep or pig; or a primate such as an ape, gorilla, orangutan, lemur, monkey or chimpanzee. A suitable mammal for prophylaxis or treatment using the pharmaceutical formulations of the invention is a human.

The pharmaceutical formulations of the invention can be administered to a mammal having a disease or condition treatable by activation of the kappa opioid receptor. Alternatively, the pharmaceutical compositions can be administered as prophylactics to a mammal having a risk of contracting or developing a disease or condition preventable by activation of the kappa opioid receptor. Diseases or conditions that can be treated or prevented by administration of the pharmaceutical compositions of the invention include, without limitation, any condition that can be ameliorated by activation of the kappa opioid receptor, including such conditions as pain, inflammation, pruritus, hyponatremia, hypokalemia, congestive heart failure, liver cirrhosis, nephrotic syndrome, hypertension, edema, ileus, tussis and glaucoma.

The invention further provides a method of treating of preventing a kappa opioid receptor-associated disease or condition in a mammal, wherein the method includes administering to the mammal a composition containing an effective amount of kappa opioid receptor agonist peptide amide in a formulation of the invention. The mammal can be any mammal, such as a domesticated or feral mammal, or even a wild mammal. Alternatively, the mammal can be a primate, an ungulate, a canine or a feline. For instance, and without limitation, the mammal may be a pet or companion animal, such as a high-value mammal such as a thoroughbred or show animal; a farm animal, such as a cow, a goat, a sheep or pig; or a primate such as an ape or monkey. In one particular aspect, the mammal is a human.

The kappa opioid receptor-associated disease, disorders or condition preventable or treatable with the kappa opioid receptor agonist peptide amide in a formulation of the invention can be any kappa opioid receptor-associated condition, including but not limited to acute or chronic pain, inflammation, pruritus, hyponatremia, edema, ileus, tussis and glaucoma. For instance, the kappa opioid receptor-associated pain can be neuropathic pain, somatic pain, visceral pain or cutaneous pain. Some diseases, disorders, or conditions are associated with more than one form of pain, e.g., postoperative pain can have any or all of neuropathic, somatic, visceral, and cutaneous pain components, depending upon the type and extent of surgical procedure employed.

The kappa opioid receptor-associated inflammation can be any inflammatory disease or condition including, but not limited to sinusitis, rheumatoid arthritis tenosynovitis, bursitis, tendonitis, lateral epicondylitis, adhesive capsulitis, osteomyelitis, osteoarthritic inflammation, inflammatory bowel disease (IBD), irritable bowl syndrome (IBS), ocular inflammation, otitic inflammation or autoimmune inflammation.

The kappa opioid receptor-associated pruritus can be any pruritic disease or condition such as, for instance, ocular pruritus (used interchangeably with the term pruritis), e.g., associated with conjunctivitis, otitic pruritus, pruritus associated with end-stage renal disease also known as uremic pruritus, where many patients are receiving kidney dialysis, and other forms of cholestasis, including primary biliary cirrhosis, intrahepatic cholestasis of pregnancy, chronic cholestatic liver disease, uremia, malignant cholestasis, jaundice, as well as dermatological conditions such as eczema (dermatitis), including atopic or contact dermatitis, psoriasis, polycythemia vera, lichen planus, lichen simplex chronicus, pediculosis (lice), thyrotoxicosis, tinea pedis, urticaria, scabies, vaginitis, anal pruritus associated with hemorrhoids and, as well as insect bite pruritus, chemotherapy-induced pruritus and drug-induced pruritus, such as mu opioid-induced pruritus.

The kappa opioid receptor-associated pruritus can be any neuopathic itch, such as for instance and without limitation, notalgia paresthetica, contact dermatitis and atopic dermatisis.

The kappa opioid receptor-associated edema can be any edematous disease or condition such as, for instance, edema due to congestive heart disease or to a syndrome of inappropriate antidiuretic hormone (ADH) secretion. Kappa opioid receptor-associated ileus can be any ileus disease or condition including, but not limited to, post-operative ileus and opioid-induced bowel dysfunction. Kappa opioid receptor-associated neuropathic pain can be any neuropathic pain, such as, for instance, trigeminal neuralgia, diabetic pain, viral pain such as herpes zoster-associated pain, chemotherapy-induced pain, nerve-encroaching metastatic cancer pain, neuropathic pain associated with traumatic injury and surgical procedures, as well as variants of headache pain that are thought to have a neuropathic component, e.g., migraine.

Kappa opioid-associated pain also includes ocular pain, such as that following photo-refractive keratectomy (PRK), ocular laceration, orbital floor fracture, chemical burns, corneal abrasion or irritation, or pain associated with conjunctivitis, corneal ulcers, scleritis, episcleritis, sclerokeratitis, herpes zoster ophthalmicus, interstitisal keratitis, acute iritis, keratoconjunctivitis sicca, orbital cellulites, orbital pseudotumor, pemphigus, trachoma or uveitis.

Kappa opioid-associated pain also includes throat pain, particularly associated with inflammatory conditions, such as allergic rhinitis, acute bronchitis, the common cold, contact ulcers, herpes simplex viral lesions, infectious mononucleosis, influenza, laryngeal cancer, acute laryngitis, acute necrotizing ulcerative gingivitis, peritonsillar abscess, pharyngeal burns, pharyngitis, reflus laryngopharyngitis, acute sinusitis, and tonsillitis.

The present invention provides a method of treating or preventing a kappa opioid receptor-associated disease or condition in a mammal, such as a human, wherein the method includes administering to the mammal a formulation of the invention comprising an effective amount of a kappa opioid receptor agonist peptide amide, and an absorption enhancer of the invention. In another embodiment the kappa opioid receptor-associated condition is pain.

In another embodiment the kappa opioid receptor-associated condition treatable with the formulations of the invention is inflammation, such as rheumatoid arthritic inflammation, osteoarthritic inflammation, IBD inflammation, IBS inflammation, ocular inflammation, otitic inflammation, autoimmune inflammation or inflammation due to a viral infection, such as inflammation due to a human influenza virus or a zoonotic influenza virus, such as the H1N1 virus that causes swine flu. Other virus infections that cause inflammation that can be treated with the kappa opioid receptor agonist formulations of the invention include inflammation caused by infection with the corona viruses: SARS-associated corona virus (Severe acute respiratory syndrome-associated virus, SARS CoV) and inflammation due to novel corona virus, nCov2 the cause of the corona virus, CoVID19 pandemic.

In still another embodiment the kappa opioid receptor-associated condition treatable with the formulations of the invention is pruritus (such as atopic dermatitis, kidney-dialysis-associated pruritus, ocular pruritus, otitic pruritus, insect bite pruritus, or opioid-induced pruritus), edema, ileus, tussis or glaucoma.

In one aspect, the pain is a neuropathic pain (such as trigeminal neuralgia, migraine, diabetic pain, viral pain, chemotherapy-induced pain or metastatic cancer pain), a somatic pain, a visceral pain or a cutaneous pain. In another aspect the pain is arthritic pain, kidney-stone pain, uterine cramping, dysmenorrhea, endometriosis, dyspepsia, post-surgical pain, post medical procedure pain, ocular pain, otitic pain, breakthrough cancer pain or pain associated with a GI disorder, such as IBD or IBS. In another aspect the pain is pain associated with surgery, wherein the surgery is pelvic laparoscopy, tubal ligation, hysterectomy and cholecystectomy. Alternatively, the pain can be pain associated with a medical procedure, such as for instance, colonoscopy, cystoscopy, hysteroscopy or endometrial biopsy. In a specific aspect, the atopic dermatitis can be psoriasis, eczema or contact dermatitis. In another specific aspect, the ileus is post-operative ileus or opioid-induced bowel dysfunction.

Another form of kappa opioid receptor-associated pain treatable or preventable with the synthetic peptide amides of the invention is hyperalgesia. In one embodiment, the method includes administering an effective amount of a synthetic peptide amide of the invention to a mammal suffering from or at risk of developing hyperalgesia to prevent, ameliorate or completely alleviate the hyperalgesia.

Kappa opioid receptor-associated pain includes hyperalgesia, which is believed to be caused by changes in the milieu of the peripheral sensory terminal occur secondary to local tissue damage. Tissue damage (e.g., abrasions, burns) and inflammation can produce significant increases in the excitability of polymodal nociceptors (C fibers) and high threshold mechanoreceptors. This increased excitability and exaggerated responses of sensory afferents is believed to underlie hyperalgesia, where the pain response is the result of an exaggerated response to a stimulus. The importance of the hyperalgesic state in the post-injury pain state has been repeatedly demonstrated and appears to account for a major proportion of the post-injury/inflammatory pain state.

In another embodiment the kappa opioid receptor-associated condition is pain, inflammation (such as rheumatoid arthritic inflammation, osteoarthritic inflammation, IBD inflammation, IBS inflammation, ocular inflammation, otitic inflammation or autoimmune inflammation), pruritus (such as atopic dermatitis, kidney-dialysis-associated pruritus, ocular pruritus, otitic pruritus, insect bite pruritus, or opioid-induced pruritus), edema, ileus, tussis or glaucoma. In one aspect, the pain is a neuropathic pain (such as trigeminal neuralgia, migraine, diabetic pain, viral pain, chemotherapy-induced pain or metastatic cancer pain), a somatic pain, a visceral pain or a cutaneous pain. In another aspect the pain is arthritic pain, kidney-stone pain, uterine cramping, dysmenorrhea, endometriosis, dyspepsia, post-surgical pain, post medical procedure pain, ocular pain, otitic pain, breakthrough cancer pain or pain associated with a GI disorder, such as IBD or IBS. In another aspect the pain is pain associated with surgery, wherein the surgery is pelvic laparoscopy, tubal ligation, hysterectomy and cholecystecomy. Alternatively, the pain can be pain associated with a medical procedure, such as for instance, colonoscopy, cystoscopy, hysteroscopy or endometrial biopsy. In a specific aspect, the atopic dermatitis can be psoriasis, eczema or contact dermatitis. In another specific aspect, the ileus is post-operative ileus or opioid-induced bowel dysfunction.

In another embodiment the kappa opioid receptor-associated condition is a kappa opioid receptor-associated condition preventable or treatable by sodium and potassium-sparing diuresis, also known as aquaresis. An example of such kappa opioid receptor-associated conditions preventable or treatable by administering a kappa opioid receptor agonist peptide amide in the formulation of the invention includes edema. The edema may be due to any of a variety of diseases or conditions, such as congestive heart disease or syndrome of inappropriate ADH secretion.

In another embodiment the kappa opioid receptor-associated condition is hyponatremia or other edematous disease. The kappa opioid receptor-associated hyponatremia or edema can be any hyponatremic or edematous disease or condition such as, for instance, hyponatremia and edema associated with congestive heart failure or to a syndrome of inappropriate antidiuretic hormone (ADH) secretion, or hyponatremia that is associated with intensive diuretic therapy with thiazides and/or loop diuretics. The synthetic peptide amides of the invention exhibit a significant sodium-sparing and potassium-sparing aquaretic effect, which is beneficial in the treatment of edema-forming pathological conditions associated with hyponatremia and/or hypokalemia. Accordingly, the synthetic peptide amides of the invention also have utility in methods of treating or preventing hyponatrenia-related conditions, examples of which are provided below. Hyponatremia-related conditions can be categorized according to volume status as hypervolemic, euvolemic, or hypovolemic.

The kappa opioid receptor-associated hyponatremia can be any disease or condition where hyponatremia (low sodium condition) is present, e.g., in humans, when the sodium concentration in the plasma falls below 135 mmol/L, an abnormality that can occur in isolation or, more frequently, as a complication of other medical conditions, or as a consequence of using medications that can cause sodium depletion.

In addition to these conditions, numerous other conditions are associated with hyponatremia including, without limitation: neoplastic causes of excess ADH secretion, including carcinomas of lung, duodenum, pancreas, ovary, bladder, and ureter, thymoma, mesothelioma, bronchial adenoma, carcinoid, gangliocytoma and Ewing's sarcoma; infections such as: pneumonia (bacterial or viral), abscesses (lung or brain), cavitation (aspergillosis), tuberculosis (lung or brain), meningitis (bacterial or viral), encepthalitis and AIDS; vascular causes such as: cerebrovascular occlusions or hemorrhage and cavernous sinus thrombosis; neurologic causes such as: Guillain-Barre syndrome, multiple sclerosis, delirium tremens, amyotrophic lateral sclerosis, hydrocephalus, psychosis, peripheral neuropathy, head trauma (closed and penetrating), CNS tumors or infections and CNS insults affecting hypothalamic osmoreceptors; congenital malformations including: agenesis of corpus callosum, cleftlip/palate and other midline defects; metabolic causes such as: acute intermittent porphyria, asthma, pneurothorax and positive-pressure respiration; drugs such as: thiazide diuretics, acetaminophen, barbiturates, cholinergic agents, estrogen, oral hypolglycemic agents, vasopressin or desmopressin, high-dose oxytocin, chlorpropamide, vincristine, carbamezepine, nicotine, phenothiazines, cyclophosphamide, tricyclic antidepressants, monoamine oxidase inhibitors and serotonin reuptake inhibitors; administration of excess hypotonic fluids, e.g., during hospitalization, surgery, or during or after athletic events (i.e., exercise-associated hyponatremia), as well as use of low-sodium nutritional supplements in elderly individuals.

Other conditions associated with hyponatremia include renal failure, nephrotic syndrome (membranous nephropathy and minimal change disease), cachexia, malnutrition, rhabdomyolysis, surgical procedures, elective cardiac catheterization, blood loss, as well as hypercalcemia, hypokalemia, and hyperglycemia with consequent glycosuria leading to osmotic diuresis.

The invention also provides a bioactive composition that includes a biologically active peptide embedded in an oligomeric saccharide forming a particle including the stabilized biologically active peptide. In one embodiment the bioactive composition that includes a biologically active peptide embedded in an oligomeric saccharide forming a particle including the stabilized biologically active peptide also includes one or more of the following: a salt of a carboxylic acid, an absorption enhancer, a binding agent, a chelating agent and a pharmaceutically acceptable carrier or excipient. The salt of a carboxylic acid can be any suitable salt of a carboxylic acid, such as but not limited to sodium citrate. The absorption enhancer can be any suitable absorption enhancer, such as for instance, sodium caprate lauroyl L-carnitine. The binding agent can be any suitable binding agent to promote cohesiveness, such as cellulose, methyl or ethyl cellulose, starch, gelatin, PVP, PEG, polyvinyl alcohols and polymethacrylates. The chelating agent can be any suitable chelating agent such as, and without limitation, succinic acid or EDTA. Commonly used pharmaceutically acceptable carriers or excipients include calcium salts, such as calcium chloride, calcium phosphate and calcium sulfate; metallic oxides, sugars, sugar alcohols and sweeteners to name a just few of those well known in the art.

The biologically active peptide can be any suitable a biologically active peptide, such as, and without limitation, a kappa opioid receptor agonist peptide. In one embodiment the a kappa opioid receptor agonist peptide can be a D-amino acid tetrapeptide amide as described in U.S. Pat. Nos. 7,402,564, 7,713,937 and 7,842,662. In one embodiment, the D-amino acid tetrapeptide amide is the kappa opioid receptor agonist compound: D-Phe-D-Phe-D-Leu-D-Lys-[ω(4-aminopiperidine-4-carboxylic acid)]-OH also referred to in the literature as CR845 (defelikefalin).

The oligomeric saccharide which coats the biologically active peptide or in which the biologically active peptide is embedded can be any suitable oligomeric saccharide, such as for instance an oligomeric saccharide such as a disaccharide. In one embodiment the disaccharide may include a glucose monomer such as dextrose. In another embodiment the disaccharide may be a glucose dimer such as trehalose.

In one embodiment the biologically active peptide is a tetrapeptide amide kappa opioid receptor agonist embedded in a composition comprising trehalose to form a particle comprising a stabilized biologically active peptide, wherein the particles have an average diameter of from about 2 microns to about 1000 microns. In another embodiment the particles have an average diameter of from about 5 microns to about 750 microns.

In another embodiment, the invention provides a bioactive composition that includes a biologically active peptide, such as the kappa opioid receptor agonist, CR845 embedded in an oligomeric saccharide forming a particle including the stabilized biologically active peptide, wherein the oligomeric saccharide includes a disaccharide such as trehalose, the 1,1-α-glycoside linked glucose dimer. Such trehalose/CR845 particles are useful as medicinal dry powders, incorporated into blends of medicinal dry powders, or compressed into tablets with solid absorption enhancers, such as lauroyl L-carnitine, and/or citric acid amongst many other well-known absorption enhancers without the use of a medium chain fatty acid, salt of a medium chain fatty acid or a medium chain fatty acid glyceride.

The invention further provides a bioactive composition including a biologically active peptide embedded in an oligomeric saccharide particle to form a stabilized biologically active peptide particle, wherein the oligomeric saccharide enhances the stability of the biologically active peptide over at least a year at 25° C. In one embodiment, the biologically active peptide is a kappa opioid receptor agonist comprising one or more D-amino acids and the oligomeric disaccharide comprises glucose. The kappa opioid receptor agonist comprising one or more D-amino acids can be any suitable kappa opioid receptor agonist, such as a tetrapeptide amide kappa opioid receptor agonist, such as for instance CR845 and the oligosaccharide can be a disaccharide comprising glucose, such as, for instance, and without limitation, the 1-1, α-linked glucopyranoside dimer, trehalose.

The bioactive composition of the invention including a biologically active peptide embedded in an oligomeric saccharide particle can be included in a pharmaceutically acceptable tablet, caplet, capsule, powder, or liquid suspension for administration as a medicament. The pharmaceutically acceptable tablet, caplet, capsule, powder, slurry or liquid suspension may further include one or more of a salt of a carboxylic acid, an absorption enhancer, a binding agent and a pharmaceutically acceptable carrier or excipient. In one embodiment the pharmaceutically acceptable tablet, caplet, capsule, powder, slurry or liquid suspension may include sodium citrate as the carboxylic acid. In another embodiment the pharmaceutically acceptable tablet, caplet, capsule, powder, slurry, or liquid suspension may include lauroyl L-carnitine as an absorption enhancer.

In a further embodiment, the pharmaceutically acceptable tablet, caplet, capsule, powder, slurry or liquid suspension may include CR845 as the a kappa opioid receptor agonist biologically active peptide embedded in an oligomeric saccharide in the form of stabilized particles having a diameter of from about 5 to about 10 microns or from about 5 to about 50 microns. In some embodiments, the oligomeric saccharide is a glucose-containing oligomeric saccharide, such as trehalose.

The formulations including the kappa opioid receptor agonist peptide amides and absorption enhancers of the invention can be administered by methods disclosed herein for the treatment or prevention of any hyperalgesic condition, such as, but without limitation, a hyperalgesic condition associated with allergic dermatitis, contact dermatitis, skin ulcers, inflammation, rashes, fungal irritation and hyperalgesic conditions associated with infectious agents, burns, abrasions, bruises, contusions, frostbite, rashes, acne, insect bites/stings, skin ulcers, mucositis, gingivitis, bronchitis, laryngitis, sore throat, shingles, fungal irritation, fever blisters, boils, Plantar's warts, surgical procedures or vaginal lesions.

Moreover, the formulations including the kappa opioid receptor agonist peptide amides and absorption enhancers of the invention can be administered by methods disclosed herein for the treatment or prevention of any hyperalgesic condition associated with burns, abrasions, bruises, abrasions (such as corneal abrasions), contusions, frostbite, rashes, acne, insect bites/stings, skin ulcers (for instance, diabetic ulcers or a decubitus ulcers), mucositis, inflammation, gingivitis, bronchitis, laryngitis, sore throat, shingles, fungal irritation (such as athlete's foot or jock itch), fever blisters, boils, Plantar's warts or vaginal lesions (such as vaginal lesions associated with mycosis or sexually transmitted diseases).

Hyperalgesic conditions associated with post-surgery recovery can also be addressed by administration of formulations including the kappa opioid receptor agonist peptide amides and absorption enhancers of the invention. The hyperalgesic conditions associated with post-surgery recovery can be any hyperalgesic conditions associated with post-surgery recovery, such as for instance, radial keratectomy, tooth extraction, lumpectomy, episiotomy, laparoscopy and arthroscopy. Hyperalgesic conditions associated with inflammation can also be addressed by administration of formulations including the kappa opioid receptor agonist peptide amides and absorption enhancers of the invention.

EXAMPLES

Example 1

Oral Administration of Dosing Formulations in Canines

The test formulation was delivered orally within a capsule in a single dose. Capsules were lubricated with reverse osmosis purified water immediately prior to administration. Animals were gently stroked along the neck to stimulate the swallowing reflex after dosing. Immediately after dosing, 5-10 mL of purified water was administered to the animal. The oral cavity was inspected following the water flush to ensure that the capsule had been swallowed.

Bioavailability of CR845 as shown used herein are calculated as follows:

$$\% f = \frac{(AUC \text{ oral/Dose oral})}{(AUC \text{ iv/Dose iv})} \times 100$$

Example 2

Bioactivity of Trehalose-Embedded CR845 Salt Prototype Formulations

Spray dried particles of CR845 acetate/trehalose/citric acid (9.8/88.2/2.2% w/w) and CR845.HCl/trehalose (23/77% w/w) were filled into intrinsically enteric (acid resistant) HPMC capsules (average particle diameter of about 5 μm; particle size distribution D(v0.1)=1.5 μm, D(v0.9)=12.1 μm) and administered to cohorts of eight canines. Citric acid added to the acetate salt was to balance the pH. Average bioavailability (% f) and standard error about the mean (SEM) for each formulation was determined as described above and shown in Table 1 below.

TABLE 1

| Formulation | % f | SEM |
| --- | --- | --- |
| CR845 acetate/trehalose/citric acid | 4 | 3.23 |
| CR845.HCl/trehalose | 10 | 6.75 |

Hereinafter, all CR845 used in the formulations described refers to the hydrochloride salt, CR845.HCl.

Example 3

Embedding of CR845 in Trehalose Particles by Spray Drying

The CR845/Trehalose composite particles were produced by preparing an aqueous solution containing the appropriate amount of the components to provide the percentages shown in Table 2, below. Solutions containing 5% solids were pumped into a laboratory scale spray dryer with 35 kg/hr of drying gas capacity at 8 grams/minute. The solutions were atomized at 10 psig into the drying gas with an inlet temperature ranging from 123° C. to 131° C. The particles were separated from the drying gas stream using a cyclone separator.

TABLE 2

| | Components (% w:w) | | | | bioavailability | |
| --- | --- | --- | --- | --- | --- | --- |
| Formulation | CR845 | Trehalose | Na Caprate | EDTA | % f | SEM |
| A | 23 | 77 | 0 | 0 | 10.2 | 2.6 |
| B | 19 | 62 | 14 | 5 | 2.3 | 1.0 |
| C | 18 | 60 | 13 | 9 | 3.2 | 1.0 |
| D | 18 | 60 | 22 | 0 | 5.8 | 1.8 |
| E | 22.5 | 67.5 | 0 | 10 | 5.8 | 2.5 |

Each of the formulation batches of composite CR845/Trehalose particles had consistent particle size distribution, purity by HPLC and water content by Karl Fischer analysis as shown in Table 3, below.

TABLE 3

| | Particle Size Distribution | | | | Analysis | |
| --- | --- | --- | --- | --- | --- | --- |
| Batch | D(v 0.1), μm | D(v 0.5), μm | D(v 0.9), μm | Span | Purity (%) | Water (wt %) |
| A | 1.5 | 5.5 | 12.1 | 1.93 | 99.3 | 2.4 |
| B | 1.6 | 6.3 | 15.1 | 2.14 | 99.5 | 2.8 |
| C | 1.6 | 6.4 | 17.0 | 2.41 | 99.2 | 3.4 |
| D | 1.5 | 5.3 | 11.5 | 1.89 | 98.9 | 2.4 |
| E | 1.4 | 5.7 | 12.3 | 1.91 | 98.8 | 3.1 |

The formulations were filled into size 3 Vcaps® Enteric Capsules (22 capsules per formulation) with a target fill weight of 5 mg CR845 per dose. The capsules were sealed across the body and head joint using an ethanolic solution of hydroxypropyl methyl cellulose acetate succinate.

TABLE 4

| Batch | Target (mg) | Average (mg) | Std. Dev. (mg) | RSD (%) | Dose |
| --- | --- | --- | --- | --- | --- |
| A | 26.3 | 26.3 | 0.1 | 0.4 | 4.94 |
| B | 35.5 | 35.5 | 0.2 | 0.6 | 5.07 |
| C | 31.2 | 31.4 | 0.6 | 2.0 | 5.07 |
| D | 26.8 | 26.7 | 0.4 | 1.6 | 5.04 |
| E | 24.0 | 24.2 | 0.5 | 1.9 | 5.39 |

Example 4

Spray Coating of CR845/HPMC onto Microcrystalline Cellulose Particles

To prepare an oral solid dose formulation, uniform spherical microcrystalline cellulose cores (Cellet® 500, 500-700

µm) were spray coated with a layer of a mixture of the API, CR845 plus hydroxypropylmethyl cellulose (HPMC), followed by addition of a layer of an enteric coating for modified release.

As an example, Batch 2 was manufactured using a Glatt GPCG-1.1 fluid bed with 6" Wurster Insert. A process air flow of 40 cubic feet per minute was set at 50° C. at the inlet. The system was charged with 756 grams of Cellet 500 particles. The drug coating solution contained 4 grams of CR845 and 40 grams of HPMC in 800 grams of purified water. The drug coating solution was sprayed as atomized droplets onto the fluidized Cellet particles using a nozzle with a 1.5 mm orifice. After spraying the entire quantity of drug coating solution the inlet air temperature was set to 25° C. and the coated particles were collected once cooled.

The formulation provided increased drug load and improved active pharmaceutical ingredient (API) recovery. See Table 5, below.

TABLE 5

| Batch | Target Drug Load (%) | Target HPMC Load (%) | Target PEG6K Load (%) | API:HPMC:PEG6000 | yield (%) | reconciliation (%) | Batch size (g) | CR845 recovery (%) | RSD* Of recovery |
|---|---|---|---|---|---|---|---|---|---|
| 001 | 0.5 | 0.5 | 0.0 | 1:1:0 | 92.3 | 99.2 | 800 | 51.2 | 0.9 |
| 002 | 0.5 | 5.0 | 0.0 | 1:10:0 | 89.4 | 99.2 | 800 | 69.2 | 1.0 |
| 003 | 1.0 | 1.0 | 0.0 | 1:1:0 | 87.2 | 100 | 1000 | 79.0 | 0.3 |
| 004 | 1.5 | 1.0 | 0.5 | 1.5:1:0.5 | 91.2 | 99.7 | 1000 | 87.7 | 0.80 |

*RSD: Relative standard deviation of recovery

Yield (%) was calculated on the basis of CR845-coated particles recovered after completion of the coating process. The reconciliation (%) included material losses on vessel walls etc. recovered after cleaning the equipment.

vessel, while continuing the mixing. The second vessel and mixer were then rinsed with 100 grams of purified water and the rinsed material added to the mixture in the first vessel. Mixing of the dispersion was continued for not less than 60 minutes after which the dispersion was passed through a U.S. Standard #35 mesh screen (0.5 mm screen) into a third vessel. 100 grams of purified water was then passed through the mesh screen into the third vessel and the Eudragit/triethyl citrate/talc dispersion mixed using a propeller mixer at a slow speed.

The CR845 drug loaded pellets were then loaded into a fluid bed dryer GPCG-1.1 with a 6" Wurster insert (See Table 6). Air was passed over the drug loaded pellets at a rate of 35-65 m³/h at 35° C. to 40° C. Atomized Eudragit/triethyl citrate/talc dispersion was applied to the pellets at a spray rate of 8 to 15 g/min.

TABLE 6

Glatt fluid bed processor GPCG 1.1 with 6" Warster insert

| Batch | Target Drug Load (%) | Target HPMC Load (%) | Target Trehalose (%) | APL:HPMC:Trehalose | % w/w Solids in Solution | Yield (%) | CR845 recovery (%) | Solid Support | Support Material |
|---|---|---|---|---|---|---|---|---|---|
| 5 | 0.5 | 0.0 | 5.0 | 1:00:10 | 10.0 | 93.2 | 55.2 | Cellet 500 | MCC |
| 6 | 0.5 | 5.0 | 5.5 | 1:10:11 | 15.0 | 94.2 | 85.0 | Cellet 500 | |
| 7 | 0.5 | 7.4 | 5.0 | 1:15:10 | 15.0 | 93.4 | 82.9 | Cellet 500 | |
| 8 | 0.5 | 7.5 | 20.8 | 1:15:42 | 32.0 | 94.2 | 88.7 | Cellet 500 | |
| 9 | 0.5 | 7.5 | 30.0 | 1:15:60 | 35.0 | 94.5 | 86.6 | Cellet 500 | |
| 10 | 0.5 | 7.5 | 20.3 | 1:15:42 | 32.0 | 94.0 | 97.4 | Suglets 500/600 | Sucralose |
| 11 | 0.5 | 7.5 | 20.3 | 1:15:42 | 32.0 | 95.1 | 100.8 | Suglets 500/600 | |

Example 5

Enteric Coating of CR845/Trehalose on Microcrystalline Cellulose or Sucralose Pellets 1923 grams Eudragit® L30 D55 polymer dispersion was added to mixing a first vessel. The suspension was stirred using a homogenizer mixer.

2146.3 grams of purified water was added to a second mixing vessel also set up with a homogenizer mixer. 57.7 grams of triethyl citrate and 288.5 grams of talc were slowly added while mixing. A uniform dispersion was produced by mixing was continued for a minimum of 10 minutes.

Contents of the mixing vessels were combined by slowly adding the triethyl citrate/talc dispersion from the second mixing vessel to the Eudragit suspension in the first mixing Example 6

Dissolution of Enteric Coated Pellets

Suglet® pellets coated with CR845 or coated with sodium caprate were enteric-coated and the percent dissolution at pH 6.8 over time was monitored. An example is shown in FIG. 1. The enteric weight gain of 50% or 100% is the increase in weight of the particle due to the enteric coating. These two enteric coatings were used to evaluate the dissolution profiles for targeting intestinal sites of absorption.

Example 7

Administration to Canines

CR845 embedded in trehalose and coated on composite particles A-E from Example 3 were administered to canines in a standard test environment and bioavailability of CR845 determined as described above. Results after administration of formulation A-E to eight animals each are shown in the DMPK graphs in FIGS. 2-6 respectively.

This application claims the benefit of U.S. Provisional Patent Application No. 62/991,560 filed 18 Mar. 2020, the entire specification of which is incorporated by reference herein.

The specifications of each of the U.S. patents and published patent applications, and the texts of the literature references cited in this specification are herein incorporated by reference in their entireties. In the event that any definition or description contained found in one or more of these references is in conflict with the corresponding definition or description herein, then the definition or description disclosed herein is intended.

The examples provided herein are for illustration purposes only and are not intended to limit the scope of the invention, the full breadth of which will be readily recognized by those of skill in the art.

The invention claimed is:

1. A formulation for oral delivery of a kappa opioid receptor agonist, the formulation comprising, particles including a kappa opioid receptor agonist and an oligosaccharide, wherein the kappa opioid receptor agonist is CR845 having the formula:

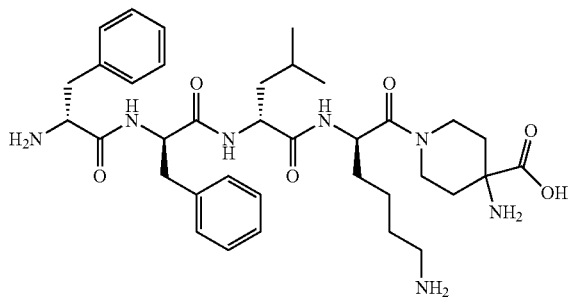

D-Phe-D-Phe-D-Leu-D-Lys-[ω(4-aminopiperidine-4-carboxylic acid)]-OH or a hydrate, salt, acid salt or acid salt hydrate thereof;

wherein the oligosaccharide is trehalose and wherein the CR845 is stable for at least a year at 25° C.

2. The formulation according to claim 1, further comprising one or more absorption enhancers selected from the group consisting of sodium caprate, lauroyl L-carnitine, and a quaternary ammonium salt.

3. The formulation according to claim 1, wherein the formulation further comprises at least one pharmaceutically acceptable component selected from the group consisting of a diluent, an excipient and a carrier.

4. The formulation according to claim 1, further comprising one or more of a salt of a carboxylic acid, an absorption enhancer, a binding agent and a chelating agent.

5. The formulation according to claim 4, wherein the salt of the carboxylic acid is a citrate salt, the absorption enhancer is lauroyl L-carnitine, and the chelating agent is ethylenediaminetetraacetic acid.

6. A pharmaceutically acceptable tablet, caplet, capsule, powder, slurry, liquid suspension or gel comprising the formulation according to claim 1.

7. The pharmaceutically acceptable tablet, caplet, capsule, or powder according to claim 6, wherein each of the tablet, caplet, capsule, or powder is enterically coated.

8. A method of manufacture of the formulation according to claim 1, the method comprising spray drying a mixture comprising a kappa opioid receptor agonist CR845 and trehalose to form particles.

9. The formulation according to claim 4, further comprising one or more absorption enhancers selected from the group consisting of sodium caprate, lauroyl L-carnitine, and a quaternary ammonium salt.

10. The formulation according to claim 9, further comprising at least one pharmaceutically acceptable component selected from the group consisting of a diluent, an excipient and a carrier.

11. The formulation according to claim 1, wherein the particles comprising the CR845 and the trehalose are in a capsule, a caplet or a powder.

* * * * *